US000001398H

United States Statutory Invention Registration [19]

[11] Reg. Number: H1398

Campbell

[43] Published: Jan. 3, 1995

[54] DNA-BASED FLUOURESCENT SENSOR

[76] Inventor: James R. Campbell, 18904 Rolling Acres Way, Olney, Md. 20832

[21] Appl. No.: 932,999

[22] Filed: Aug. 21, 1992

Related U.S. Application Data

[63] Continuation of Ser. No. 635,019, Dec. 28, 1990, abandoned.

[51] Int. Cl.[6] ..... C12Q 1/68; C12Q 1/00

[52] U.S. Cl. ..... 435/6; 935/77; 935/78

[58] Field of Search ..... 435/6, 7; 935/77, 78

[56] References Cited

U.S. PATENT DOCUMENTS 4,486,539 12/1984 Ranki et al. ..... 436/504
4,777,129 10/1988 Dattagupta et al. ..... 435/6

OTHER PUBLICATIONS

Kemp et al. P.N.A.S. 86:2433 (1989).
Bahtia et al. SPIE. 1054: 184 (1989).
Kemp et al. P.N.A.S. 86:2423–27 (1989).
Bahtia et al. Chem. Abstracs. Abstrac NO. 111, 53497; VIII (1989).
Syvänen A. Medical Biology 64:313–324 (1986).
Meinkoth et al. Anal. Biochem. 138:267–84 (1984).
Colorimetric detection of specific DNA segments amplified by polymerase chain reactions, David J. Kemp et al., Proc. Natl. Acad. Sci. USA. vol. 86, pp. 2423–2427, Apr. 1989 Medical Sciences.
Fiber Optic–Based Immunosensors: A Progress Report, Suresh K. Bhatia et al., SPIE, vol. 1054, Fluorescence Detection III (1989), pp. 184–190.

*Primary Examiner*—Shean Wu

[57] ABSTRACT

The fluorescent detection of target DNA is enhanced by amplifying the DNA in a sample by initiating a polymerase chain reaction using a first pair of primers and an appropriate polymerase. The DNA is then reamplified, this time using a second pair of nested primers which bracket DNA base sequences within the region bracketed by the first set of primers. At least one of the second pair of primers is bound to a fluorescent reporter molecule and at least one of the second pair of primers has bound thereto a specific binding site for a double-stranded DNA-binding protein. The thus amplified sample is then contacted with a fluorescent sensor having the appropriate double-stranded DNA-binding protein attached thereto. Then, the fluorescent reporter molecule is excited by light of the appropriate wavelength. The present invention provides greater sensitivity, adaptability and ease of use than previously available.

4 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

DNA-BASED FLUOURESCENT SENSOR

The present application is a continuation application of U.S. Ser. No. 07/635,091, filed, Dec. 28. 1990, now abandoned.

BACKGROUND OF THE INVENTION a. Field of the Invention

The present invention relates generally to biosensors, and more particularly to fluorescence-based biosensors that incorporate polymerase chain reaction (PCR) technology.

b. Description of the Prior Art

The detection of pathogens in air, water, and food, as well as in biological samples, has been of great interest. Tests that detect the presence of and identify a pathogen are also useful in detecting and countering the use of biological weapons. Most commercial systems for the detection of pathogens rely on antibody-based systems. These systems, while useful, have limited sensitivity and are more vulnerable to neutralization by changes in the surface antigenicity of the organism than the lesser used nucleic acid-based detection systems. Probes for nucleic acids can also detect the presence of foreign genes that have been introduced into a different host.

DNA-based detection systems detect a specific pathogen by detecting DNA fragments unique to that pathogen. Additionally, the detection of DNA can be useful in forensic medicine.

Kemp et al, Proc. Natl. Acad Sci. USA, 86 pp 2423–2427 (1989) (incorporated by reference herein), describe a colorimetric scheme for the detection of DNA from a specific organism. DNA from the target organism is amplified in the sample by a process such as PCR using an appropriate homologous primer pair for the DNA sequence to be amplified. Then, the amplified target DNA is further amplified, this time using modified new primers to produce amplified blunt-ended DNA having affinity binding ligands at both ends. The blunt-ended DNA is then affinity bound at one end to a substrate, such as a microtiter dish precoated with an affinity reagent, and at the other end to an enzyme, for example by biotin-avidin bonding. A chromogenic substrate is then added to the dish and allowed to react. The absorbance is then read, for example in a microtiter plate reader. This enzyme-linked assay, while useful, requires considerable work and special equipment. Additionally, the format of the assay makes the detection of multiple different microorganisms difficult.

Fluorescence-based biosensors, relying on antibodies for detection, were known before the present invention, as described in Bhatia et al "Fiber Optic-based Immunosensors: A Progress Report", SPIE Vol. 1054 Fluorescence Detection III (1989), the entirety of which is incorporated herein by reference. Nevertheless, to date, no one has developed a fluorescent sensor-based system for DNA detection using PCR.

SUMMARY OF THE INVENTION

Accordingly, it is an object of this invention to detect target DNA using a simple and easy to use system. The target is very small amounts of DNA or organisms in environmental or medical samples, or residual DNA contaminating bacterial fermentation products.

Accordingly, it is another object of the present invention to detect target DNA in less than one hour.

Accordingly, it is a further object of the present invention to detect target DNA with great sensitivity and reduced vulnerability to neutralization by genetically engineered changes in the target microorganism.

Accordingly, it is still another object of the present invention to detect the target of a plurality of multiple, different microorganisms simultaneously.

Accordingly, it is still another object of the present invention to incorporate a sensor device whose exposed surface for detection of target DNA is either a glass or plastic waveguide, or a membrane such as nitrocellulose or PVDF.

These and additional objects of the invention are accomplished by amplifying the target DNA using a pair of appropriate primers, (i.e., a pair of short (about 18 nucleotides or bases) DNA single strands), then amplifying the previously amplified DNA using "nested" primers which bracket (i.e., delimit) a region of DNA within the region bracketed by and amplified using the first primer pair. The nested primers have been modified so that at least one of the nested primers contains a specific binding site for a double-stranded DNA-binding protein (dsDNA-BP) and at least one of the pair of nested primers has a fluorescent reporter molecule (FRM) covalently attached thereto. The dsDNA-BP is attached to the surface of a fluorescent sensor by adsorption or covalent interation.

In an assay, the amplification (typically about one million-fold) of the target DNA with concomitant inclusion of both the fluorophores and dsDNA binding site, makes the amplified portion the only DNA detectable by the sensor. The amplified target DNA, with the FRM and the dsDNA-BP binding site attached thereto, will specifically bind with the dsDNA-BP on the sensor. This binding brings the FRM close to the surface of the fluorescent sensor, where it can be excited. For sensors such as evanescent wave based systems, the close proximity of the FRM to the surface of the sensor enhances both the excitation of the FRM, as well as the coupling of the energy emitted by the excited FRM (at a wavelength different than that of the excitation energy) back into the sensor. For sensors whose exposed binding surface employs a membrane, e.g. in dipstick or slide format, the binding of the fluorescent DNA by the dsDNA-BP permits it to be manipulated in separation steps or for introduction into fluorometric devices. At the photodetector, the signal is discriminated and interpreted by a microprocessor. The entire excitation, emission, detection and interpretation process can occur in microseconds.

DESCRIPTION OF THE PREFERRED EMBODIMENTS

Samples suspected of containing microorganisms or characteristic DNA are processed as appropriate (centrifugation, addition of lysing agents, or no processing) to obtain a crude preparation which contains at least a fraction of any target DNA that may be present in the sample. The sample can be from any source. For example, the sample can be environmental (such as air, water, soil, surface swipes) or biological (blood, urine, feces, etc.).

The target DNA from the crude preparation is then amplified by the polymerase chain reaction. The polymerase chain reaction is a well-known generalized procedure for amplifying target DNA. The polymerase chain reaction is described in Saiki et al, Science, 230, 1350–1354 (1985), and Saiki et al, Science, 239, 487–491

(1988), both of which are incorporated herein by reference. In general, a sample of the crude preparation is added to an aqueous solution containing an enzyme appropriate for PCR (such as Taq polymerase or Q-beta replicase) appropriate buffers, deoxyribonucleotide triphosphates, and two primers.

The thus prepared reaction mixture is then thermally cycled at three successive temperatures:

1. A high temperature (usually about 94° C.), at which the two strands of the double stranded target DNA melt, or denature, and separate into single strands.
2. A low temperature (37°–54° C.), at which the primers bind (anneal) to their homologous regions on the single stranded target DNA.
3. An intermediate temperature (about 72° C.) at which the Taq polymerase binds to the DNA-primer complex and moves down the single stranded target, copying it and making a duplicate second strand. The exact temperatures for each of the steps must be determined empirically for the particular DNA to be amplified, although optimum conditions can be estimated, based on certain characteristics of the DNA. It is also possible to carry out a *two*-step temperature cycle wherein the third (72° C.) step described herein is eliminated. This is because in heating from the second (37°–54° C.) step directly back to the first (94° C.) step the reaction passes through the 72° C. range over a period of time which, although brief, can be sufficient to allow complete primer extension to occur.

This thermal cycle is then repeated until the target DNA has been amplified sufficiently to permit its detection. Typically, the thermal cycle is repeated about 20 to 30 times, resulting in an approximately one million-fold amplification of the target DNA.

The thus amplified target DNA is then subjected to a second, briefer amplification. This second amplification uses a second pair of primers that are nested within the region bracketed by the first set of primers. In other words, the second pair of primers is complementary to, and binds with, sites on the amplified DNA within the region bracketed by the first set of primers.

The second primers also differ from the first primers in that at least one member of the second pair has attached covalently to its 5′ end, a fluorescent reporter molecule, (e.g., FITC fluorescein isothiocyanate, TRITC tetramethyl rhodamine isothiocyanate, Rhodamine, Texas Red). In addition, at least one member of the second primer pair has covalently attached to its 5′ end a particular DNA fragment that constitutes a specific binding site for a double-stranded DNA binding protein (dsDNA-BP). Typically, the dsDNA-BP is attached to one member of the primer pair and the FRM is attached to the other member of the primer pair. Nevertheless, it is possible to covalently bind both the dsDNA-BP binding site and the FRM to only one of the primers and leave the other primer unmodified. This is accomplished by designing one primer with the dsDNA-BP binding site covalently attached to the 5′ end of the primer, and the FRM covalently attached to the 5′ end of the binding site. In an evanescent wave detection format, this modification may result in greater sensitivity of the system by bringing the FRM closer to the surface of the optical fiber, for more efficient excitation and more efficient coupling of emitted light back into the fiber. The second amplification is typically shorter than the first amplification and need only be sufficient to ensure that the concentration of twice-amplified DNA, which contains the fluorescent reporter molecule and the double stranded DNA-binding protein, will emit a detectable level of fluorescence energy when the DNA is bound to the sensor and excited by light of an appropriate wavelength.

A dsDNA-BP is attached to a fluorescent sensor by any means appropriate for fixing a protein to the exposed portion of the material of the sensor. Several techniques have been used to attach proteins to various substrates and these techniques may also be useful in the present invention. Typically, the substrate for the dsDNA-BP is made of glass or membrane material and the dsDNA-BP is attached using a technique appropriate for the fixing of a protein to glass or synthetic membranes such as nitrocellulose or PVDF. One technique for immobilizing protein on glass which is particularly useful in the present invention is described by Bhatia et al, id.

The exposed surface of the sensor having the dsDNA-BP immobilized thereon is then exposed to the twice amplified DNA preparation, which, if it originally contained the target DNA, now contains the amplified target DNA with reporter molecules and dsDNA-BP binding site attached. Any target DNA amplified with the second set of primers will then bind, via the dsDNA binding site, to the dsDNA-BP immobilized on the exposed surface of the sensor. If the sensor is an optical waveguide, the evanescent wave excites the fluorescent reporter molecule, which has been positioned in close proximity to the outer surface of the sensor via binding of the dsDNA-BP with the dsDNA-BP binding site on the DNA. The fluorescence of the excited fluorescent reporter molecule, at a wavelength different from that of the excitation energy, is also readily coupled back into the sensor, which detects the fluorescent emission by known means. If the exposed surface of the sensor is a membrane, the dsDNA-BP is attached to the membrane either by adsorption or by covalent linkage, and unreacted sites on the membrane are blocked by any of several blocking reagents. The twice-amplified DNA is then applied to the membrane, where it binds to the attached protein via the binding site incorporated into the amplified DNA. The membrane is then introduced into a fluorometer, typically via a dipstick or slide device, and fluorescence intensity measured.

Several dsDNA-BP's are known to exist and can be used according to the present invention.

A fluorescent sensor useful according to the present invention can be any one having an exposed surface of a material onto which a dsDNA-BP can be immobilized. Typically, the sensor will have an exposed surface made of a silica-based glass or a plastic, but other materials such as nitrocellulose or PVDF membrane may also be used. The geometry of the waveguide, membrane, or other surface is not critical to the present invention.

Because the primer pair for at least the first amplification step has been selected to be homologous to base sequences unique to the target DNA, only the target DNA is amplified. Because the target DNA is greatly amplified (about one million-fold), the amplified target DNA becomes essentially the only DNA in the sample preparation after the first amplification step has been completed. Thus, spurious amplification of DNA other than target DNA, in the critical second amplification step wherein the binding site and FRM are introduced, is essentially avoided. Fluorescence of an intensity below the threshold level could be attributed to the background of free fluoresceinated primers. However free fluoresceinated primers lack the binding site and thus cannot be concentrated close to the sensor surface, in the region of the evanescent wave. Any fluorescent emissions from free primers thus will be essentially undetectable.

The selection of a portion of DNA from a target organism for amplification, rather than the detection of the entire organism itself, permits the present invention to detect harmful organisms that have been genetically engineered. In particular, the present invention is well-suited to the detection of DNA that directs the production of a toxin. For example, the primers may be selected to amplify a unique region of a botulism toxin gene over one million-fold. The present invention will then detect the presence of any microorganism containing the gene and thus potentially capable of producing the botulism toxin, regardless of whether the gene for that toxin was naturally present in the organism or whether the gene was inserted into the organism by genetic manipulation.

Also, fermentation products are typically contaminated by DNA from the producing microorganism. The present invention can detect the use of biologically produced toxins by detecting this DNA contamination. The present invention is also applicable to the detection of unwanted microbes in commercial fermentation processes (unwanted bacteria and fungi in beer fermentation) and can be used in industrial food processing and environmental water monitoring to detect microbial contamination (e.g., fecal contamination of well or ground water and *Clostridium botulinum* contamination of food).

Additionally, the present invention provides a useful clinical diagnostic tool that can detect infection via the presence of viral or bacterial DNA in blood or tissue samples, and can quickly (typically in 1.5 to 2 hrs) screen for well-defined markers which suggest the presence of genetic defects. Additionally, the present invention can be used to detect RNA (such as from RNA viruses). This is accomplished by first producing a complementary DNA (cDNA) copy of an RNA sequence unique to the target organisms, through the use of reverse transcriptase enzyme. The cDNA is then processed using the identical PCR-based system described herein. The sensitivity of the present invention is typically greater than 10,000 times that of other existing clinical techniques. Also, the present invention can detect the presence in a pathogen of genes encoding resistance to a variety of antibiotics, thus providing clinically important data on antibiotic sensitivity much faster than currently available by any existing laboratory methods, which rely on first culturing the organisms (days to weeks) then testing cultures for sensitivity.

Moreover, as individual primers are "invisible" to and do not interact with each other, several different sets of primers can be used simultaneously in the same reaction tube to probe a sample for multiple pathogens. By attaching different FRM to the different primer sets, the presence of multiple different microorganisms can be discriminated. This technique provides a unique capability for simultaneous multi-organism detection , which is not available in other detection formats.

Having described the invention, the following examples are given to illustrate specific applications of the invention including the best mode now known to perform the invention. These specific examples are not intended to limit the scope of the invention described in this application.

EXAMPLES

Detection of *Escherichia coli* in an aqueous sample (bacterial culture media).

Materials and Methods

Known dilutions of *E. coli* were added in 10 μl aliquots to a standard polymerase chain reaction (PCR) mixture, prepared according to manufacturer's instruction (Amplitaq Kit, Perkin Elmer Cetus, Emeryville, Calif.). The two oligonucleotide primers (5μl each) for the reaction were 18 mers, homologous to regions at each end of a 1 kb fragment of DNA that represented the tetracycline resistance gene in the bacterium. The reaction was carried out under the following conditions: 94° C. for 1 min, 54° C. for 1 min, and 74° C. for 1 min, and this three-step procedure was repeated for 30 cycles.

At the end of this PCR reaction, 5 μl of each of two new primers were added to the mix, and the PCR was continued for another 10 cycles. The new primers were homologous to regions on the tetracycline resistance gene located within the region bracketed by the first set of primers. Covalently bound to the 5′ end of one of these second primers was a fluorescein molecule, and covalently bound to the 5′ end of the other primer was a "universal binding site," comprised of a 10 base sequence that represents a specific binding site for a double stranded DNA binding protein (dsDNA BP).

After the second PCR, a 10 μl aliquot of the reaction mix was placed in a well of a 0.7% agarose gel, electrophoresed at 120 v for 30 min, stained with ethidium bromide and observed under UV illumination.

Five μl of the reaction mix was then mixed with an equal volume of methanol, placed on a PVDF disk on a plastic dipstick and incubated for 30 min at 37° C. in a humidified chamber. The PVDF disks had been previously prepared by coating them with 10 μl of a 100 μg/ml solution of dsDNA BP for 1 hr at 37° C. in a humidified chamber, followed by a brief rinse in phosphate buffered saline (PBS), pH 7.4, and blocking with 0.25% BLOTTO in 6X SSC (Maniatis, 1990) for 15 min at 37° C.

The treated dipsticks were then introduced into a FIAX fluorometer, and specifically bound fluoresence was measured. Alternatively, a glass optical fiber was coated with the dsDNA BP as above and the fiber was then treated with the PCR mix. A laser pulse was transmitted down the fiber to excite specifically bound fluorescent molecules, and the emission energy was captured by the fiber and measured by a microprocessor.

The ethidium stained gel revealed a single band in the correct molecular weight range, indicating successful amplification of the target DNA starting with as few as a single bacterium. Studies using radiolabelled dsDNA BP revealed good binding of the protein to PVDF and to glass. The amplified DNA containing the binding site for the dsDNA BP successfully bound to the immobilized protein, and optimization studies for this reaction are in progress.

As shown above, the successful amplification of target DNA from a single bacterium, using the technique according to the present invention, has been demonstrated in an ethidium stained gel. Binding of this amplified, modified target DNA to a sensor surface via the dsDNA BP has been demonstrated via fluorescence analysis. Thus, each of the two steps required for the present invention, specific amplification of target DNA and the binding of the modified and amplified target DNA to a sensor surface via a double stranded DNA-binding protein, have been demonstrated.

Obviously, many modifications and variations of the present invention are possible in light of the above teachings. It is therefore to be understood that, within the scope of the appended claims, the invention may be practiced otherwise than as specifically described.

What is claimed is:

1. A method for the fluorescent detection of target DNA, comprising the steps of:

a) performing a first amplification on a sample suspected of containing said target DNA by initiating a polymerase chain reaction with a first pair of primers, which delimit therebetween a first region of DNA base sequences of said target DNA to be amplified by said amplification, and a polymerase which catalyzes said polymerase chain reaction, said amplification being sufficiently great that the amount of DNA other than target DNA in the amplified sample is negligible in comparison to the amount of target DNA in the amplified sample if target DNA were present in the unamplified sample;

b) performing a second amplification on the amplified sample using a second pair of primers, said second pair of delimiting therebetween a second region of DNA base sequences within the first region of DNA base sequences bracketed by said first pair of primers and selected for amplification by said first amplification using said first pair of primers, at least one member of said second pair of primers having a fluorescent reporter molecule bound thereto and at least one member of said second pair of primers having a specific binding site for a double-stranded DNA-binding protein bound thereof, thereby producing an amount of double stranded, fluorescent reporter molecule-bound and double stranded DNA-binding protein site-bound, twice amplified DNA which, when excited at an excitation frequency of said reporter molecule, emits a detectable level of fluorescence if target DNA was present in the unamplified sample;

c) contacting at least an aliquot of said twice amplified sample with a fluorescent sensor comprising a fiber waveguide having attached to its exposed surface a double stranded CNA-binding protein which binds to said double stranded DNA-binding protein site on said twice amplified DNA;

d) exciting the fluorescent reporter molecule bound to any of said twice amplified DNA bound to said sensor via said double stranded CNA-binding protein with light of an excitation wavelength for said reporter molecule;

e) detecting any fluorescent emission from said excited fluorescent reporter molecule.

2. The method of claim 1, wherein said bound reporter molecule is excited with said light in the form of an evanescent wave along said sensor, and wherein the energy emitted by said bound reporter molecule is coupled back into said sensor.

3. The method of claim 1, wherein said reporter molecule is selected from the group consisting of fluorescein isothiocyanate, tetramethyl rhodamine isothiocyanate, rhodamine and texas red.

4. The method of claim 1, wherein said sensor is a glass optical fiber.

* * * * *